United States Patent
Ma

[11] Patent Number: 6,012,325
[45] Date of Patent: Jan. 11, 2000

[54] METHOD AND APPARATUS FOR MEASURING METALLIC IMPURITIES CONTAINED WITHIN A FLUID

[75] Inventor: Ce Ma, Apex, N.C.

[73] Assignee: The BOC Group, Inc. (a Delaware Corporation), New Providence, N.J.

[21] Appl. No.: 08/964,615

[22] Filed: Nov. 5, 1997

[51] Int. Cl.$^7$ .................................................. G01N 23/223
[52] U.S. Cl. ...................... 73/24.02; 73/24.03; 73/24.06; 73/28.04; 378/47; 378/48
[58] Field of Search .................... 73/61.72, 24.03, 73/24.02, 28.04, 31.03, 31.05, 31.07, 24.06; 422/91; 250/364, 363.01; 378/47, 48, 49, 45

[56] References Cited

U.S. PATENT DOCUMENTS

| | | | |
|---|---|---|---|
| H188 | 1/1987 | Thomson et al. ........................ | 378/45 |
| 3,443,092 | 5/1969 | Carr-Brion et al. . | |
| 4,544,386 | 10/1985 | Trayford, III et al. .................... | 55/270 |
| 5,014,287 | 5/1991 | Thornton et al. .......................... | 378/45 |
| 5,563,929 | 10/1996 | Connolly et al. .......................... | 378/51 |

*Primary Examiner*—Michael Brock
*Attorney, Agent, or Firm*—David M. Rosenblum; Salvatore P. Pace

[57] ABSTRACT

A method and apparatus for measuring metallic impurities within a fluid by X-ray fluorescence in which a sample stream flowing at a constant flow rate is passed through a microporous filter. The microporous filter contains substantially no metallic impurities and is configured to adsorb the particulate solid phase and vapor phase of the compounds. Excitation of the metallic compounds by X-ray produces an X-ray florescence having an intensity that can be measured. The change in intensity is compared with that produced by a calibrated inflow of a standard gas sample to derive the impurity concentration. In a preferred embodiment, the filter is housed within a chamber having a window that is preferably fabricated from Beryllium so as not to appreciably attenuate the X-rays.

11 Claims, 1 Drawing Sheet

METHOD AND APPARATUS FOR MEASURING METALLIC IMPURITIES CONTAINED WITHIN A FLUID

BACKGROUND OF THE INVENTION

The present invention relates to a method of measuring metallic impurities contained within a fluid and an apparatus for subjecting such a fluid to an X-ray fluorescence analysis to conduct the measurement. More particularly, the present invention relates to such a method and apparatus in which both solid and vapor phases of the metallic impurities are adsorbed in microporous filter and such filter is subjected to the on-line analysis.

Metallic impurities gases used in the fabrication of semiconductor devices can have major deleterious effects on semiconductor production. Such impurities arise because gases and liquids used within the fabrication of semiconductors are extremely corrosive. Examples of such gases are hydrogen chloride, hydrogen bromide, boron trichloride, tungsten hexaflouride and chlorine. Liquids include hydrogen bromide, hydrogen chloride, boron trichloride and chlorine. In any event, such corrosive special gases when passing through distribution systems such as tubing and chambers react with metal to produce such metallic impurities as $FeCl_3$, $ZrCl_4$, $HgCl_2$, and $MoF_6$ and $UF_6$. All of such impurities have a vapor pressure as high as about 1 Torr below 200° C. so that in the course of semiconductor fabrication, such impurities will exist in both solid and vapor forms. Thus, there exists the need to continually monitor a gas distribution system or the output of a cylinder containing such a corrosive special gas.

The prior art has recognized the monitoring requirement in U.S. Pat. No. 5,618,996. In this patent, a fluid sample stream is passed through two membrane filters situated in series. The first filter is maintained at room temperature to adsorb the particle impurities. The second filter is maintained at cryogenic temperatures to freeze out the vapor phase of the impurities. After sampling is completed, the sampling apparatus is disconnected from the facility at which the measurements are to be conducted and transported to an analysis location where analysis can be completed by ICPMS (Inductively Coupled Plasma Mass Spectrometer). As can be appreciated, the method and device of this patent can not be used to continuously sample the feed and to measure metallic impurities on-line. Moreover, a cryogenic liquid, such as liquid carbon dioxide must be on hand in order for the equipment to perform its sampling function.

As will be discussed, the present invention provides a method and apparatus that can be used to sample a stream for particulate and vapor phases of metallic impurities on a continuous basis and without the requirement of providing cryogenic fluids.

SUMMARY OF THE INVENTION

The present invention provides a method of measuring the metallic impurities contained within a fluid and comprising at least one metallic compound. In accordance with the method, a sample stream composed of the fluid is metered so that the sample stream flows at a constant flow rate. The sample stream is then passed through a microporous filter containing substantially no metallic impurities and configured to adsorb both solid and vapor phases of the at least one metallic compound. The at least one metallic compound is excited by X-ray radiation after having been absorbed within the microporous filter so that an X-ray fluorescence is produced. A change in intensity of the X-ray fluorescence is measured over at least one time period. The change in intensity is compared with that produced by a calibrated flow of a standard gas sample containing a calibrated amount of the least one metallic compound. In such manner, the concentration of the metallic impurity can be derived.

As will discussed, the change in observed intensity can be quantified by calculating the time rate of the change in intensity and dividing the result by the constant flow rate of the gas sample to produce a quotient. Such quotient would be the slope of a curve of intensity vs. time for a given flow rate. This quantity of quotient could then be compared with the result produced by a standard sample stream having a known concentration of the impurity of interest to determine the concentration of the metallic compound in the sample gas being studied.

In another aspect, the present invention provides an apparatus for subjecting a fluid to a X-ray fluorescence analysis thereby to measure impurities contained within the fluid and comprising at least one metallic compound. The apparatus comprises a metering means for metering a sample stream composed of the fluids so that the sample stream flows at a constant flow rate. A housing is provided having a chamber, an inlet to the chamber in communication with the metering means and an outlet. A microporous filter containing substantially no metallic impurities and configured to adsorb the at least one metallic compound in both solid and vapor phases is positioned within the chamber so that the sample stream passes from the inlet to the outlet and through the filter and the least one metallic impurity is adsorbed within the microporous filter. A window is provided to the chamber. The window is at least substantially transparent to X-rays so that X-rays passing through the window excite the at least one metallic compound after having been adsorbed within the microporous filter and an X-ray fluorescence is produced that is detectable outside the chamber. An X-ray source of the X-rays is positioned so that the X-rays pass into the window and impinge on the microporous filter to excite the at least one metallic compound. A detector is positioned to detect X-ray florescence outside of the chamber and is configured to measure intensity of the X-ray fluorescence. As can be appreciated, the apparatus can be used to perform the method outlined above.

BRIEF DESCRIPTION OF THE DRAWINGS

While the specification concludes with claims distinctly pointing out the subject matter that Applicant regards as his invention, it is believed that the invention will be better understood when taken in conjunction with the accompanying drawings in which:

DETAILED DESCRIPTION

Figure 1:
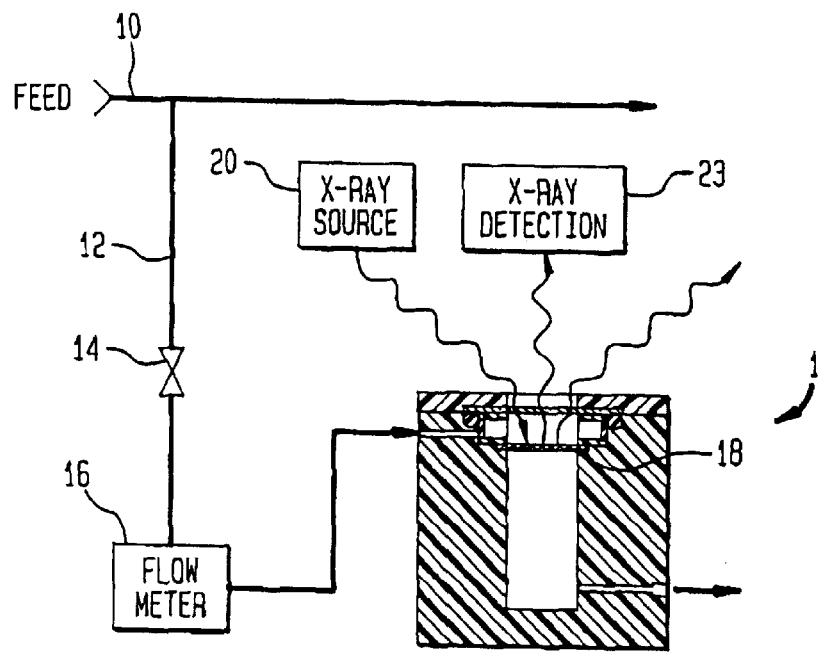
FIG. 1 is a schematic view of an apparatus used in carrying a method in accordance with the present invention.

With reference to FIG. 1, an apparatus in accordance with the present invention is illustrated. A part of a feed stream 10 is diverted as a sample stream 12 upon opening a valve 14. Sample stream 12 then passes through a flow meter 16 which can be a rotometer or alternatively, a mass flow controller. The flow of the sample stream is then adjusted so that constant known flow rate is produced. The sample stream then passes through a microporous filter 18 in which particulate and vapor phases of the metallic impurities are adsorbed.

An X-ray source 20 excites one or more metallic compounds adsorbed within microporous filter 18 so an X-ray fluorescence is produced. The X-ray fluorescence is measured in counts by an X-ray detector 22 as a function of X-ray Energy. The peaks in the measured spectra correspond to the metallic impurities that have been adsorbed within microporous filter 18. These counts are measured over one or more known time intervals. The gross counts and the emission energies can then be graphed to determine the constituents within the sample stream. Count intensity can then be correlated with the count intensity produced by a calibrated flow of a standard gas sample containing a calibrated amount of the compounded interest. The elemental concentration of the impurity can then be determined by simply taking the slope or time rate of change in intensity over the time period. As discussed above, if such slope is divided by the known constant flow rate, the resultant quotient can be compared with that produced by the calibrated standard gas sample containing the impurity of interest and the elemental concentration of the impurity within the gas sample can be derived. As can be appreciated, temperature can be an important variable. As such, the temperature at which the standard gas is measured will set the temperature at which measurements of sample stream 12 are conducted.

Obviously, the methodology discussed above can be done continuously by continually measuring counts over various energy levels after the elapse of time periods. Furthermore measurements can be conducted on-line and in real time, during gas usage. If the method, however, is conducted intermittently, then the concentration produced in the last measurement must be subtracted because obviously the measured concentration would increase over time. In this regard, a point would eventually be reached at which microporous filter 18 would have to be discarded.

Figure 2:
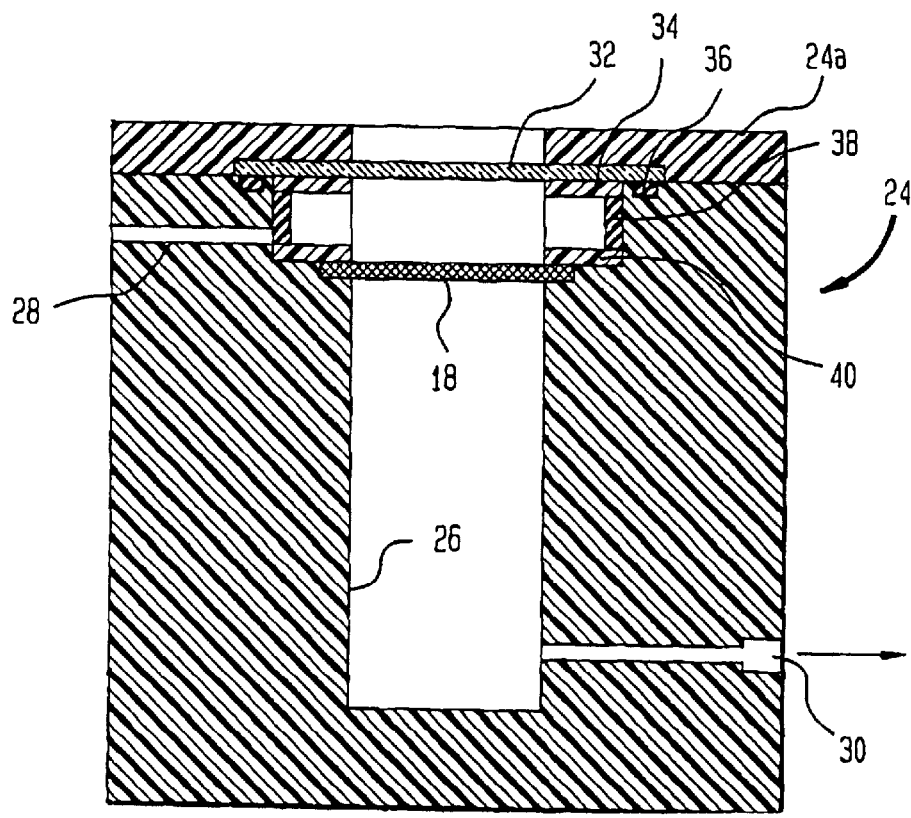
FIG. 2 is a sectional, elevational view of a sample cell used in the apparatus of FIG. 1.

With additional reference to FIG. 2, microporous filter 18 is contained within a housing 24, preferably fabricated from inert polymeric materials and which contains a chamber 26. An inlet 28 to chamber 26 is provided in communication with a flow meter 16 to introduce sample stream 12 into chamber 26 and pass the same through filter 18 at a known flow rate. The gas sample after passing through filter 18 is then discharged from outlet 30. After discharge, the simple stream can either be destroyed or refined for recovery and reuse.

Microporous filter 18 is so named in order to distinguish it from a membrane filter of the prior art. In a microporous filter, adsorption occurs within the filter itself rather than at the surface as would occur in a thin membrane filter of the prior art. Such a membrane filter will not be effective to internally adsorb the vapor phase of the metallic impurities of interest here. More specifically, microporous filter 18 should preferably have pores of about 2 microns or less. Additionally, microporous filter 18 can be fabricated from a polymer such as PEEK or TEFLON. Additionally, a high molecular weight polyethylene is another possibility. Preferably, the thickness of microporous filter 18 should be selected so as to be capable of internally adsorbing the vapor. The thickness can be about 1.6 mm. and is preferably in a range of between about 1.0 mm and about 2.3 mm. The diameter of microporous filter 18 will depend upon the flow. In this regard, experimental filters having a diameter in a range of between about 0.3 cm. and about 2.4 cm. have been successfully tested.

X-rays penetrate chamber 26 and therefore filter 18 by means of a window 32. Window 32 should be designed so as not substantially attenuate X-rays. While a minimum degree of attenuation is preferred it can be stated that window 32 should preferably attenuate no more than 10% the incoming X-rays. Window can be fabricated from Beryllium having a thickness of about 0.254 mm. with a TEFLON coating of about 1 micron. The TEFLON coating greatly reduces Helium leak rate and increase corrosion resistance of the Beryllium material.

It is to be noted that window 32 and microporous filter 18 are held in place in a gas tight relationship within housing 24 by means of a lid portion 24a of housing 24 that bears against a top washer 34. An O-ring 36 is provides a gas tight seal. Top washer 34 in turn bears against a compression ring 38 that also bears against a bottom washer 40. Lid portion 24a of housing is held in place, bearing against top washer 34, by means of a set of machine screws (not shown) that are threaded into bores provided within housing 24. Chamber 36 can be separately vented to a pressure relieve valve or the flow to housing 24 can be provided with a pressure relieve valve to prevent over pressures from damaging window 32.

Source 20 and detector 22 can advantageously be any one of a number of portable units that include an X-ray source of between about 14 and about 22 KEV, such as $Cm^{244}$ or $Cd^{109}$. The detector is preferably a solid state silicon-lithium detector. In place of a portable unit, Source 20 can be an X-ray tube and detector 22 can be a stand-alone proportional detector.

As an example, a standard sample stream of $BCl_3$ containing a metallic impurity of $FeCl_3$ in a known elemental iron concentration of about 5 µg/L or 5 ppb was passed through a microporous filter 18 at a flow rate of about 0.8 liters/min. The microporous filter 18 was fabricated from a disc of PEEK having a diameter of about 0.3 cm. and a thickness of about 1.6 mm. The pore size of the material was about 2.0 micrometers. The flow time was about 10 minutes. A time rate of change in counts of about 300 was produced. When this time rate of change was and when divided by the flow rate of 0.8, a quotient of about 37.5 was derived. A calibration constant k of about 0.13 µg/counts was then obtained by taking the ratio of the known concentration of about 5 µg/L and the quotient of about 37.5. As will be shown, the calibration constant k can be used to compare the "quotient" of an unknown sample with the quotient of the standard sample stream. The metallic impurity within a gas sample with a different elemental iron concentration was then quantified. This gas sample had a flow rate of about 1.0 L/min. The time rate of change of counts taken over a time period of about 10 minutes was found to be 600 to produce a quotient (derived by dividing such time rate of change by the flow rate) of about 60.0. The elemental iron concentration of such gas stream sample was then computed to be about 8.0 µg/L or about 8 ppb by taking the product of the calibration constant k (0.13) and the quotient (60).

While the present invention has been described with reference to a preferred embodiment, as will occur to those skilled in the art, numerous changes additions and omissions may be made without departing from the spirit and scope of the present invention.

I claim:

1. A method of measuring metallic impurities contained within a gas and comprising at least one metallic compound, said method comprising:

metering a sample stream composed of said gas so that said sample stream flows at a constant flow rate;

passing the sample stream through to an microporous filter containing substantially no metallic impurities, the microporous filter having micropores and a thickness selected so as to adsorb both solid and vapor phases of said at least one metallic compound; and exciting said at least one metallic compound by X-ray radiation after having been adsorbed within said microporous filter so that an x-ray florescence is produced;

measuring a change in intensity of said x-ray florescence over at least one time period; and comparing said change in intensity with that produced by a calibrated flow of a standard gas sample containing a calibrated amount of said at least one metallic compound.

2. The method of claim 1, wherein said change in intensity is compared to that of said calibrated flow by calculating a time rate of said change in intensity, dividing the result of said calculation by the constant flow rate of the sample stream to produce a quotient, and comparing said quotient with that produced by said calibrated flow of said standard gas to quantify a concentration of said at least one metallic compound within said sample stream.

3. The method of claim 2, wherein said time rate of change in intensity is continually measured over a plurality of said time periods to continually quantify said concentration.

4. The method of claim 1 or claim 2 or claim 3, wherein said microporous filter comprises PEEK or TEFLON.

5. The method of claim 4, wherein said microporous filter has micropores of no greater than about 2 microns.

6. An apparatus for subjecting a gas to an x-ray fluorescence analysis thereby to measure impurities contained within said gas and comprising at least one metallic compound, said apparatus comprising:

metering means for metering a sample stream composed of said gas so that said sample stream flows at a constant flow rate;

a housing having chamber, an inlet to said chamber in communication with said metering means, an outlet, a microporous filter containing substantially no metallic impurities, the microporous filter having micropores and a thickness selected so as to adsorb said at least one metallic compound in both solid and vapor phases, the microporous filter positioned within said chamber so that said sample stream passes from the inlet to the outlet and through said filter and said at least one metallic compound is adsorbed within said microporous filter, and a window to said chamber, the window being formed of Beryllium coated with TEFLON so as to be at least substantially transparent to x-rays to allow said x-rays to pass through said window, excite said at least one metallic compound after having been adsorbed within said microporous filter, and to produce an x-ray fluorescence detectable outside of said chamber;

an x-ray source of said x-rays positioned so that said x-rays enter said window and impinge on said microporous filter to excite said at least one metallic compound; and a detector positioned to detect x-ray fluorescence outside of said chamber and configured to measure intensity of said x-ray fluorescence.

7. The apparatus of claim 6, wherein said microporous filter comprises PEEK or TEFLON.

8. The apparatus of claim 7, wherein said microporous filter has micropores of no greater than about 2 microns.

9. The apparatus of claim 8, wherein said microporous filter has a thickness in a range of between about 1.0 mm and about 2.3 mm.

10. The apparatus of claim 6, wherein said x-ray source is a radioisotope.

11. The apparatus of claim 6, wherein said Beryllium has a thickness of about 0.254 mm. and said TEFLON has a thickness of about 1 micron.

* * * * *